US008223445B2

(12) United States Patent
van den Engh

(10) Patent No.: US 8,223,445 B2
(45) Date of Patent: Jul. 17, 2012

(54) LENS POSITIONING APPARATUS

(75) Inventor: Ger van den Engh, Seattle, WA (US)

(73) Assignee: Cytopeia, Seattle, WA (US)

( * ) Notice: Subject to any disclaimer, the term of this patent is extended or adjusted under 35 U.S.C. 154(b) by 190 days.

(21) Appl. No.: 12/872,869

(22) Filed: Aug. 31, 2010

(65) Prior Publication Data

US 2011/0069492 A1 Mar. 24, 2011

Related U.S. Application Data

(60) Provisional application No. 61/244,209, filed on Sep. 21, 2009.

(51) Int. Cl.
*G02B 7/02* (2006.01)
(52) U.S. Cl. ........................................ 359/813; 359/822
(58) Field of Classification Search .................. 359/813, 359/819, 821, 822, 694, 695, 793; 362/284; 385/37; 65/392, 507; 356/338
See application file for complete search history.

(56) References Cited

U.S. PATENT DOCUMENTS

| 3,823,321 A | 7/1974 | Von Rauch |
| 4,498,766 A | 2/1985 | Unterleitner |
| 4,989,977 A | 2/1991 | North, Jr. |
| 5,591,980 A | 1/1997 | Ogasawara et al. |
| 5,768,035 A | 6/1998 | Grassens et al. |
| 6,385,370 B1 * | 5/2002 | Paek et al. ........................ 385/37 |
| 6,683,831 B2 | 1/2004 | Tanaka et al. |
| 7,787,197 B2 | 8/2010 | Chen |

OTHER PUBLICATIONS

J.E. Josselin de Jong et al. "Alignment and Focusing Unit for Dual-Laser Excitation in the Fluorescence-Activated Cell Sorter," Cytometry, vol. 5: 657-659 (1984).

* cited by examiner

*Primary Examiner* — Loha Ben
(74) *Attorney, Agent, or Firm* — Douglas A Petry

(57) ABSTRACT

The present invention provides an optical analyzer having illumination optics that include a light source, such as a laser or other source, adapted to emit a collimated, or approximately collimated, light beam, and a focusing lens that focuses the beam onto a focus spot within a detection region, wherein the focusing lens is mounted in a lens positioning apparatus that allows for precise positioning of the focus spot within the detection region. The lens positioning apparatus comprises a lens holder adapted to rotate through a small angle around a pivot axis parallel to the optical path, such that the lens holder rotates in a plane perpendicular to the optical path, and an actuator adapted to provide an angular displacement of the lens holder around the pivot axis. The lens holder holds the focusing lens at a first distance from the pivot axis, and is coupled to the actuator at a second distance from the pivot axis, wherein the second distance is larger than the first distance.

5 Claims, 3 Drawing Sheets

LENS POSITIONING APPARATUS

BACKGROUND OF THE INVENTION

1. Field of the Invention

The present invention relates to the field of optics and, in particular, to laser optics, as used in optical analyzers, such as flow cytometers.

2. Description of Related Art

Particle analyzers, such as flow and scanning cytometers, are well known analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, detection is carried out using a multiplicity of photodetectors, one for each distinct dye to be detected. Both flow and scanning cytometers are commercially available from, for example, BD Biosciences (San Jose, Calif.). A description of flow cytometers is provided in Shapiro, 2003, Practical Flow Cytometry, $4^{th}$ ed. (John Wiley and Sons, Inc. Hoboken, N.J.), and in the references cited therein, all incorporated herein by reference.

In a typical flow cytometer, the excitation light from a laser or other source is focused onto a focal spot to illuminate the core stream (the fluid stream containing the particles to be analyzed). Accurate focusing of the excitation light beam on the core stream is important for optimizing focal spot intensity and, thus, fluorescence sensitivity. Optimal performance is compromised if the focused light beam is not properly adjusted on the core stream, and flow cytometers typically include one or more devices for adjusting the positioning of the focused light beam on the core stream. Because a typical flow cytometer is designed to analyze biological cells or particles that are few microns in size, the precision of the light beam adjustment also needs to be in the micron range, thus requiring high resolution mechanical displacement devices. Conventional positioning methods typically employ expensive differential micrometers to position the light source itself or optical elements, such as mirrors or prisms.

U.S. Pat. No. 4,989,977 describes a device for the accurate adjustment of the focused excitation beam on the core stream. Repositioning of the focal point is achieved using a transparent glass plate located between the focusing lens and the core stream. The glass plate, when positioned at an angle to the beam path, displaces the focal point by refracting the beam. In a multi-laser instrument, the glass plate typically is positioned between the focusing lens and the core stream, and all beams in a multi-laser instrument are passed through the single plate.

U.S. Patent Publication no. US 2009/0073579 describes another device for the accurate adjustment of the focused excitation beam on the core stream. A movable beam-adjusting lens having a long focal length lens is positioned in the optical path upstream of the focusing lens. Repositioning of the focal point is achieved by adjusting the upstream movable beam-adjusting lens. The sensitivity of the focus spot positioning to adjustments of the beam-adjusting lens position depends on the focal length of the beam-adjusting lens; the longer the focal length of the beam-adjusting lens, the less sensitive the position of the focus spot is to changes in the position of the beam-adjusting lens. The decreased sensitivity allows the use of less expensive, less precise lens positioning mechanisms, such as simple screw-type positioning systems, to obtain precise positioning control over the beam focus spot.

BRIEF SUMMARY OF THE INVENTION

The present invention provides illumination optics for use in an optical analyzer that includes a light source that emits a collimated, or approximately collimated, beam, and a focusing lens that focuses the beam onto a focus spot. The focusing lens is mounted in lens-positioning apparatus that allows repositioning of the lens in a plane perpendicular to the optical path of the beam, and allows precise positioning of the focus spot of the focused light beam.

The lens positioning apparatus comprises a lens holder adapted to rotate through a small angle around a pivot axis parallel to the optical path, such that the lens holder rotates in a plane perpendicular to the optical path. The lens holder holds a focusing lens at a radius $R_1$ from the pivot axis. An actuator adapted to provide an angular displacement of the lens holder around the pivot axis is coupled to the lens holder at a radius $R_2$ from the pivot axis, wherein $R_2 > R_1$. Preferably, $R_2$ is $\geq 2 \cdot R_1$; more preferably, $R_2$ is $\geq 3 \cdot R_1$.

Precise adjustment of the focus spot in a flow cytometer requires only minor adjustment of the position of the focusing lens, typically a movement that is small relative to the size of the focusing lens. The adjustment will be effected by a minor rotation of the lens holder, typically not more than a few degrees. The width of the focusing lens is sufficiently larger than the width of the collimated beam such that beam passes through the lens after repositioning.

In a preferred embodiment, the actuator is, or contains, an actuator screw that is linearly extended or retracted by rotation of the screw. The tip of the actuator screw is coupled to the lens holder through a magnetic coupling. A magnet or a mass of magnetically responsive material is positioned on the lens holder, and a magnet or a mass of magnetically responsive material is positioned at the tip of the actuator screw, such that the tip of the actuator screw is coupled to the lens holder.

At least one of the magnet and magnetically responsive material is shaped such that the contact point between the tip of the actuator screw and the lens holder is essentially a point on the axis of rotation of the actuator screw. Preferably, the tip of the adjusting screw is spherical or conical, and the surface of the lens holder at the point of contact is flat. The actuator screw is thus free to rotate around this contact point. This coupling advantageously provides a low friction coupling, which minimizes the forces that need to be applied to the actuator screw to make an adjustment of the lens position.

The lens and lens holder will be oriented such that a line that passes through the pivot axis and the center of the lens will be approximately perpendicular to the desired direction of adjustment of the lens. In a flow cytometer, this line will be approximately parallel to the direction of the flow (sample) stream, as the desired direction of adjustment typically is across the width of the flow stream.

In one preferred embodiment, the lens and the actuator coupling are position on opposite sides of the pivot, and the lens holder is essentially a lever with the lens attached to one arm and the actuator coupled to the opposite, longer arm. In this embodiment, the angle formed from the center of the lens to the pivot axis to the point of coupling with the actuator is about 180 degrees. In an alternative embodiment, the lens and the actuator coupling are on the same side of the pivot axis, with the lens held in between the pivot axis and actuator coupling, in which case the angle formed from the center of the lens to the pivot axis to the point of coupling with the actuator is about zero. In general, the lens holder can be adapted to couple to the actuator anywhere along a circle of radius $R_2$, centered around the pivot axis, i.e., the angle formed from the center of the lens to the pivot axis to the point of coupling with the actuator this angle can be any angle. In practice, the placement of the actuator coupling is a design choice that will depend on the placement of other instrument components. For example, in a sorting flow cytometer, there typically are additional optical components for monitoring droplet formation in the sample stream immediately downstream of the detection region. To minimize crowding of components, a lens holder configuration that places the actuator components upstream of the detection region, away from the droplet formation region, is preferable.

The present invention further provides an optical analyzer incorporating the illumination optics of the present invention, adapted to focus an illumination beam onto a sample analysis region. The optical analyzer will further comprise detection optics for measuring the light emitted from the analysis region. In a preferred embodiment, the optical analyzer is a flow cytometer, and the sample analysis region is a sample detection region in a fluid stream containing particles to be optically analyzed. Typically, the detection optics detect illumination light scattered by particles in the flow stream, as well as fluorescent light emitted by the particles after being excited by the illumination light.

The present invention provides several advantages properties for use in adjusting the position of a focus spot in a flow cytometer.

The lens holder holds a focusing lens at a radius $R_1$ from the pivot axis, and the actuator is coupled to the lens holder at a radius $R_2$ from the pivot axis, wherein $R_2 > R_1$. The use of a pivoting lens holder, with the lens position at a smaller radius from the central axis than the actuator coupling, results in a decrease in displacement of the lens movement for a given displacement of the actuator coupling point. This decreased sensitivity to movement of the focusing lens allows the use of less expensive, less precise actuator mechanisms, such as simple screw-type actuator, to obtain precise positioning control over the beam focus spot. For example, using an screw-type actuator have 100 threads per inch (tpi), the control over the lens positioning is equivalent to using a 300 tpi screw-type adjuster directly connected to the lens.

The magnetic coupling of the tip of the actuator screw to the lens holder provides a minimal friction coupling. In previously described devices using adjustment screws, the element that is adjusted typically is held against the screw by use of a spring, which not only increases the friction between the screw and the element, but also imposes a constant force against the screw threads that increase the friction of turning the screw. The magnetic coupling of the present invention not only allows for free rotation of the screw around the point of contact with the lens holder, but also minimizes the friction of turning of the screw.

The lens positioning apparatus preferably is used in a flow cytometer as components of the illumination (excitation) optics to accurately position the focus spot on a detection region within the particle stream. It typically is the case that routine adjustment of the focus spot is required only across the width of the sample stream, i.e., in a direction perpendicular to the axis of the flow stream. The lens holder preferably is oriented such that a line that passes through the pivot axis and through the center of the lens is approximately parallel to the flow stream. An angular displacement of the lens holder moves the lens along an arc having a center at the pivot axis. For small angular displacements, the lens path is approximately along a line perpendicular to the optical path and to the flow stream, as the deviation of the arc path from a line tangent to the arc path is negligible for small displacements.

In a preferred embodiment, the optical analyzer of the present invention is a flow cytometer and the beam-adjusting optics, used to adjust the illumination light focused on the detection region of the flow stream. However, fine control over the focus spot of a illumination beam can be useful in a variety of applications, and the present invention will be generally useful in applications in which fine control over the focus spot of a illumination beam in a single direction is useful. Other applications in which the illumination optics of the present invention may be useful include, for example, microscopy and laser scanning cytometry.

Figure 1:
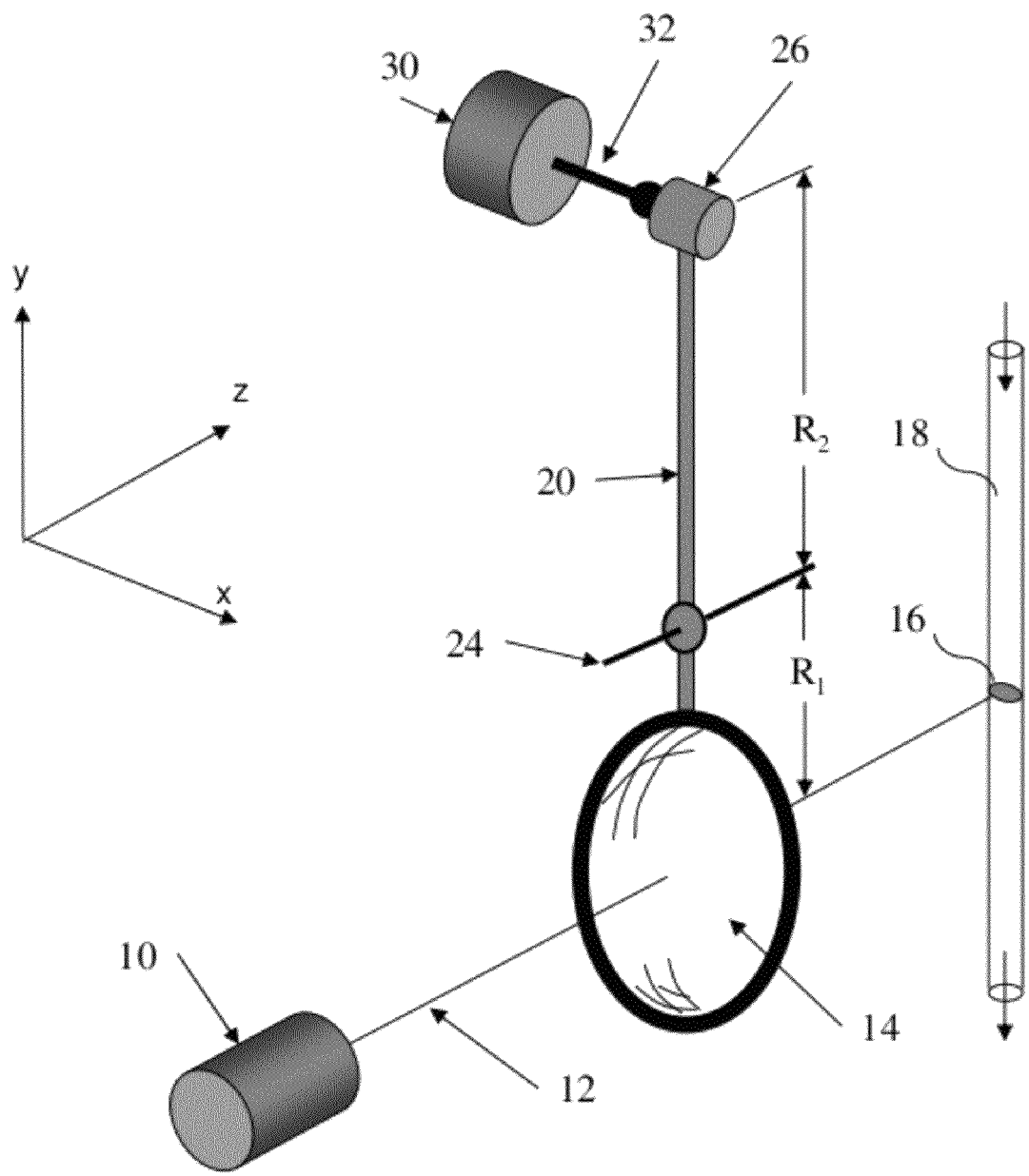
FIG. 1 shows a schematic representation of an embodiment of the illumination optics of the present invention.

The figures depict schematic representation of optical systems and components and are not drawn to scale.

DETAILED DESCRIPTION OF THE INVENTION

The illumination optics (also referred to as excitation optics) of the present invention include a light source, such as a laser or other source, adapted to emit a collimated, or approximately collimated, beam, a focusing lens that focuses the beam onto a focus spot, and a lens positioning device adapted to position the focusing lens in the light path and to allow for precise positioning of the focus spot of the focused light beam. The lens positioning device of the present invention comprises a lens holder adapted to rotate through a small angle around a primary pivot axis parallel to the optical path, such that the lens holder rotates in a plane perpendicular to the optical path. The lens positioning device further comprises an actuator coupled to the lens holder and adapted to provide an precisely controlled angular displacement of the lens holder around the pivot axis.

Light Source

Light sources suitable for use in optical analyzers are well known in the art and commercially available from a large number of sources. Example include lasers, arc lamps, and light emitting diodes. For use in the present invention, the emitted light beam should be collimated or approximately collimated. It will be understood that the light source may include collimating optics. A discussion of light sources for use in flow cytometry can be found in, for example, Shapiro, 2003, Practical Flow Cytometry, $4^{th}$ ed. (John Wiley and Sons, Inc. Hoboken, N.J.), incorporated herein by reference.

Lens Holder

The lens holder holds a focusing lens at a radius $R_1$ from the pivot axis and is adapted to allow small rotations of the holder around the pivot axis. The lens holder can be fabricated from any suitable material, such as metal or plastic. The lens holder preferably includes a central hole for mounting the holder on a cylindrical post that serves as an axle for rotation.

Angular displacement (i.e., rotation) of the lens holder around the pivot point results in repositioning of the lens in a plane perpendicular to the light path. The size of the movable focusing lens will be sufficiently larger than the width of the collimated beam such that the beam passes through the movable lens when the lens is repositioned.

In flow cytometer, the desired adjustment of the lens typically is along a line perpendicular to the flow stream, such that the focus point is adjusted along the width of the stream. To achieve this motion of adjustment, the lens hold is oriented such that a line that passes through the pivot point and the center of the lens is approximately parallel to the flow stream, such that an angular displacement of the lens holder in either direction results almost entirely of a displacement of the lens along a path perpendicular to the flow stream.

Focusing Lens

Focusing lenses are a standard elements well-known in the art and commercially available from a large number of sources. The particular lens design used in the present invention will be application-dependent, and one of skill in the art will be able to select a suitable focusing lens routinely following the guidance provided herein. A discussion of focusing lenses for use in flow cytometry can be found in, for example, Shapiro, 2003, Practical Flow Cytometry, $4^{th}$ ed. (John Wiley and Sons, Inc. Hoboken, N.J.), incorporated herein by reference. Typically, lenses are fabricated of fused silica for maximum light transmission, although any suitable material may be used.

Typically, and as exemplified herein, a focusing lens consists of a single element, more typically a single spherical lens. However, more complex focusing optics can be used. For example, crossed cylindrical lenses having different focal lengths have been used in flow cytometers to focus a laser beam to an elliptical spot on the sample stream.

The focusing lens may be mounted in the lens holder such that the plane of the lens is coplanar with the plane of rotation of the lens holder, perpendicular to the optical path. Alternatively, the focusing lens may be mounted such that the plane of the lens is not perpendicular to the optical path, such that the lens also reshapes the beam cross section (see, for example, U.S. Pat. No. 4,498,766).

The illumination optics can contain addition optical elements, such as additional lenses, prisms, or mirrors, that are involved in the focusing, shaping, and redirecting of the beam. The additional elements may be positioned either upstream or downstream in the optical path.

Actuator

The actuator is adapted to provide an angular displacement (minor rotation) of the lens holder. The actuator is coupled to the lens holder at a radius $R_2$ from the pivot axis, wherein $R_2 > R_1$. By positioning the actuator coupling at a greater radius from the pivot than the lens, the effect of actuator movement on the lens movement is decreased by the ratio of the radii. In other words, a displacement of the actuator coupling of arc length $d_A$ results in a displacement of the lens of arc length $d_L$, wherein $d_L = d_A \cdot (R_1/R_2)$. This reduction in sensitivity enables precise control and adjustment of the lens position using a less precise actuator motion.

In a preferred embodiment, the actuator is, or contains, an actuator screw that is linearly extended or retracted by rotation of the screw. The actuator screw is coupled to the lens holder through the tip of the actuator screw. The linear movement of the screw tip is in a direction perpendicular to the adjustment arm of the lever. The actuator screw can be a manually adjustable screw. Alternatively, the control of the actuator screw can be automated and controlled through appropriate electronics, using well known methods.

In preferred embodiments, the actuator is magnetically coupled to the lens holder. A magnet or a mass of magnetically responsive material is positioned on the lens holder, and a magnet or a mass of magnetically responsive material is positioned on a movable element of the adjusting device, such that the movable element of the adjusting device is coupled to the distal end of the adjustment arm.

In a preferred embodiment, the actuator is, or contains, an actuator screw and the tip of the actuator screw is magnetically coupled to the lens holder. Either the tip of the actuator screw or the lens holder where it contacts the actuator screw tip is shaped such that the contact point between the tip of the actuator screw and the lens holder is essentially a point on the axis of rotation of the actuator screw. Preferably, the tip of the adjusting screw is spherical or conical, and the surface of the lens holder at the point of contact is flat. The actuator screw is thus free to rotate around this contact point. This coupling advantageously provides a low friction coupling, which minimizes the forces that need to be applied to the actuator screw to make an adjustment of the lens position.

Description Based on the Figures

While this invention is satisfied by embodiments in many different forms, shown in the drawings and described herein in detail are preferred embodiments of the invention, with the understanding that the present disclosure is to be considered as exemplary of the principles of the invention and is not intended to limit the invention to the embodiments illustrated.

FIG. 1 shows a schematic representation of an embodiment of the illumination optics of the present invention. Sample stream 18 contains particles to be optically analyzed. For ease of description, it is arbitrarily assumed that the sample stream is oriented such that the particles move in a vertical direction. Light source 10, which typically is a laser, emits an essentially collimated beam having an optical path 12 that is focused by focusing lens 14 to focal spot 16. Focal spot 16 corresponds to the detection region in sample stream 18.

Lens holder 20 is adapted to pivot around axis 24. Lens holder 20 is adapted to hold focusing lens 14 at a radius $R_1$ from axis 24 (measured from the center of focusing lens 14). A magnet 26 is attached to the end of lens holder 20 opposite the lens at a radius $R_2$ from axis 24.

Actuator 30 contains an actuator arm 32 that can be extended or retracted. The actuator arm is coupled to magnet 26 through the tip of the actuator arm. The shape of the tip of actuator arm 32 facing magnet 26 is spherical, such that the contact between actuator arm 32 and magnet 26 is a point on the spherical face along the lengthwise axis of actuator arm 32. This allows actuator arm 32 to rotate freely around the contact point between actuator arm 32 and magnet 26.

In FIG. 1, focusing lens 14 is depicted positioned such that optical path 12 passes through the center of the lens. In this configuration, the light beam is focused onto focal spot 16, shown centered on the sample stream 18. Extension or retraction of actuator arm 32 causes a rotation of lens holder 20 around axis 24, which results in a transverse displacement of focusing lens 14. This transverse displacement of the focusing lens results in an equivalent displacement of the focal spot.

Figure 2:
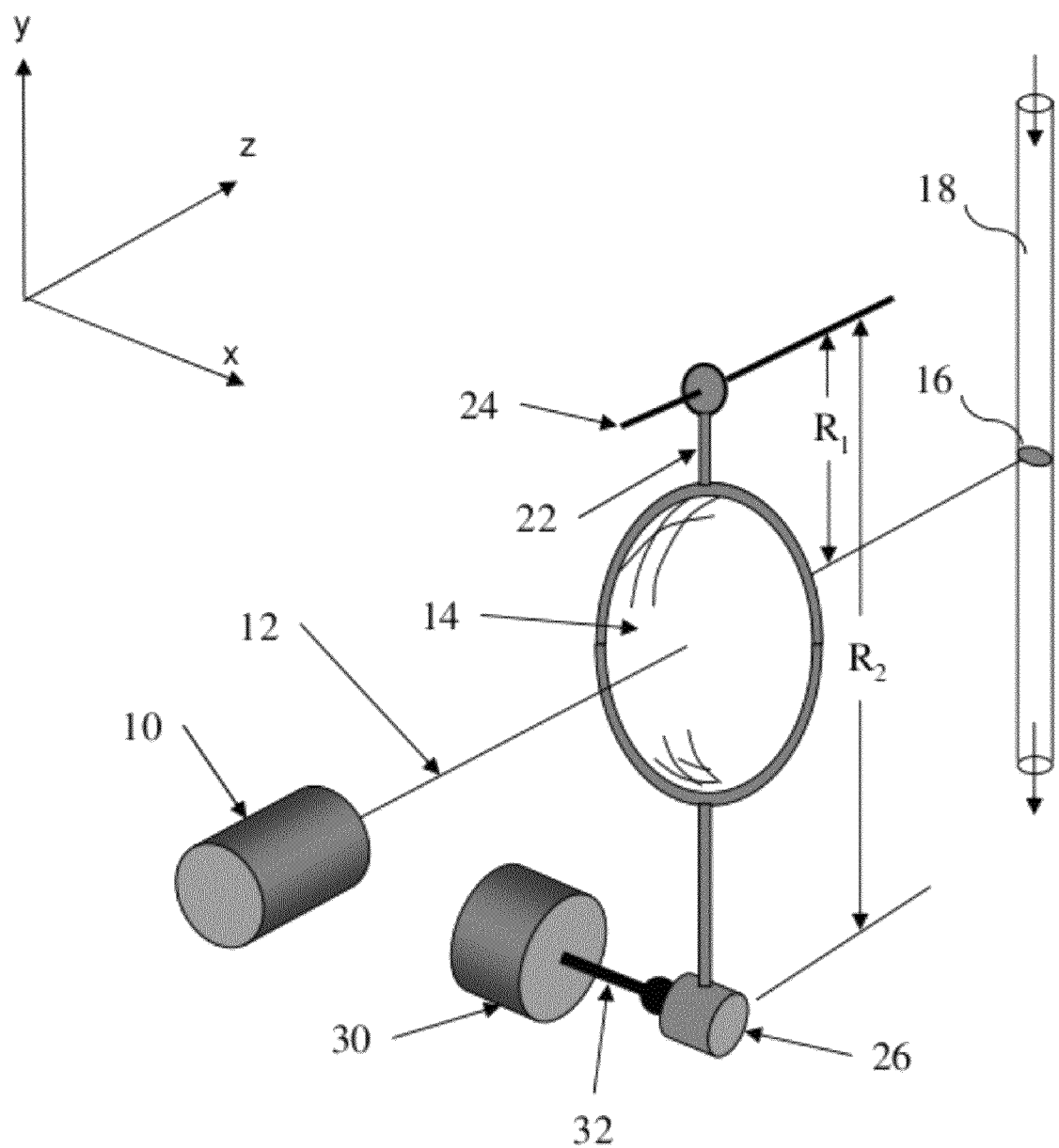
FIG. 2 shows a schematic representation of an alternative embodiment of the illumination optics of the present invention.

FIG. 2 shows a schematic representation of a variant of the embodiment shown in FIG. 1. In this embodiment, a lens holder 22 is adapted to hold both the focusing lens 14 and the magnet 26 in-line on the same side of the axis 24. All other components are as described in FIG. 1. In this embodiment shown in FIG. 2, the angle formed from axis 24 to the center of focusing lens 14 and to the center of magnet 26 is zero. In contrast, in the embodiment shown in FIG. 1, the corresponding angle is 180 degrees.

Although FIGS. 1 and 2 depict the focusing optics as a single focusing lens, more complex optics containing additional optical elements may be used, such as optics having multiple lens elements and, optionally, beam shaping optics, such as described in U.S. Pat. No. 4,498,766 and U.S. Patent Application Publication No. 2006-0256335, both incorporated herein by reference.

Figure 3:
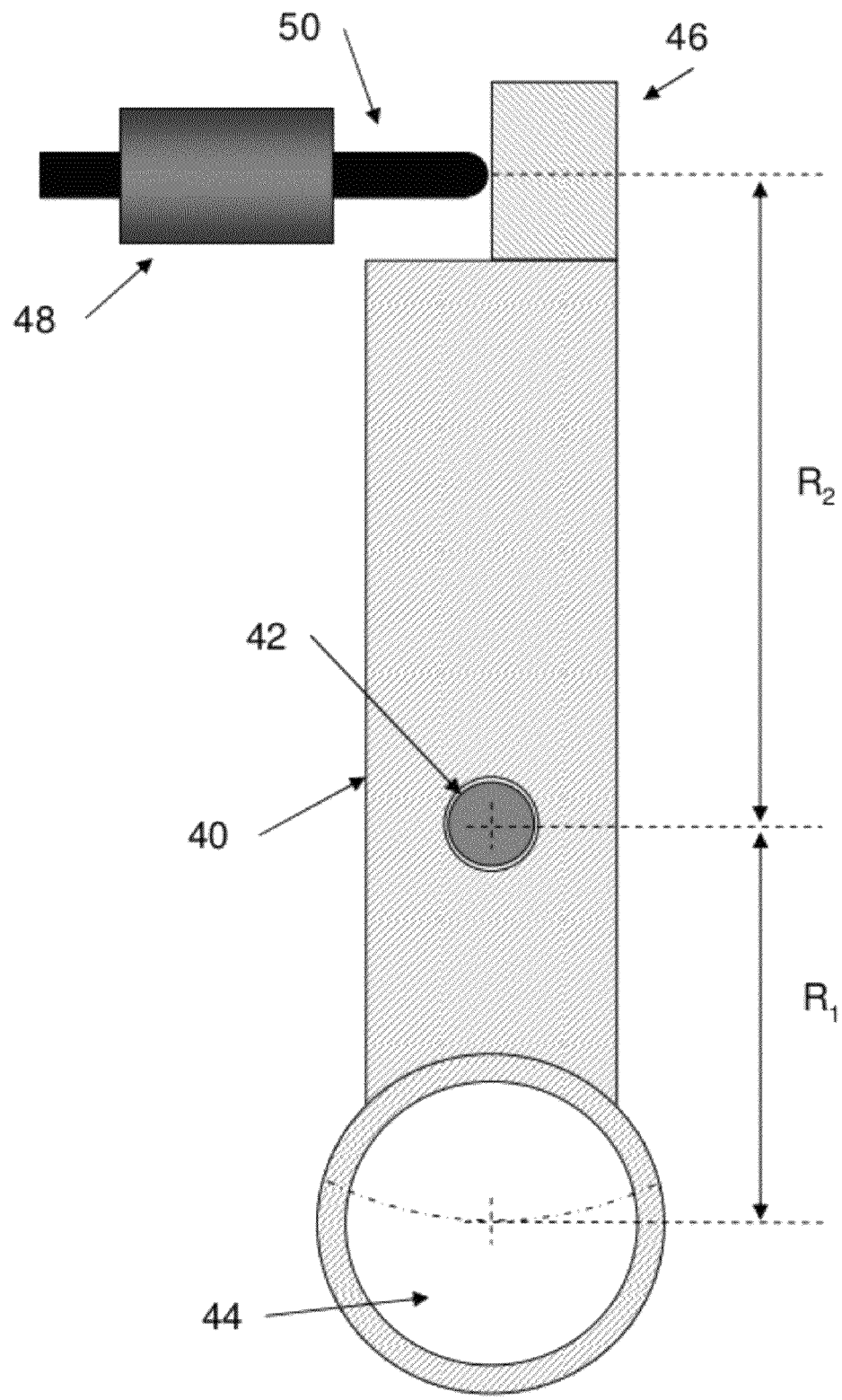
FIG. 3 shows a schematic representation of an embodiment of the lens positioning apparatus of the present invention.

FIG. 3 shows another embodiment of the lens positioning device of the invention, shown along the optical axis (corresponding to axis z in FIGS. 1 and 2).

Lens holder 40 is adapted to rotate around pivot 42. Lens holder 40 is adapted to hold focusing lens 44 at a radius $R_1$ from pivot 42, as measured from the center of focusing lens 44 to the center of pivot 42. A magnet 46 is attached to the end of lens holder 40 opposite the lens at a radius $R_2$ from pivot 42, as measured from the actuator contact point to the center of pivot 42.

Actuator 48 contains an actuator arm 50 that can be extended or retracted. The actuator arm is coupled to magnet 46 through the tip of the actuator arm. The shape of the tip of actuator arm 50 facing magnet 46 is spherical such that the contact between actuator arm 50 and magnet 46 is a point on the spherical face along the lengthwise axis of actuator arm 50. In embodiments wherein the actuator arm is a screw-type actuator, the actuator arm rotates around this lengthwise axis of rotation. This allows actuator arm 50 to rotate freely around the contact point between actuator arm 50 and magnet 46.

As actuator arm is extended or retracted, lens holder 40 is rotated around pivot 42, and lens 44 is displaced in a plane perpendicular to the axis of pivot 42. The arc-shaped path of displacement is indicated by the dotted line. As can be seen, for very small displacements, the vertical displacement of lens 44 is negligible and the displacement is essentially horizontal. The optical effect of displacement of focusing lens 44 is to displace the focal spot of the light beam on the sample stream (not shown in FIG. 3) by an amount equal to the displacement of the lens. The lens holder is oriented relative to the path of the sample stream such that the essentially horizontal displacement of the lens corresponds to a displacement of the focusing spot across the width of the sample stream, perpendicular to the direction of flow.

This reduced sensitivity of the focal spot adjustment to movement of the beam-adjusting lens enables obtaining a high degree of precision over the adjustment of the focal spot using less expensive lens adjusting mechanisms with less precise motion control.

We claim:

1. An optical analyzer comprising:
   (a) a light source adapted to emit a collimated or approximately collimated light beam along an optical path;
   (b) a focusing lens positioned in the optical path, adapted to focus the light beam onto a focal spot within a sample analysis region;
   (c) a lens holder adapted to rotate through an angle around a pivot axis parallel to the optical path, such that the lens holder rotates in a plane perpendicular to the optical path, wherein said focusing lens is mounted in said lens holder at a first radius, $R_1$, from said pivot axis;
   (d) an actuator adapted to provide an angular displacement of the lens holder around the pivot axis, wherein said actuator is coupled to said lens holder at a second radius, $R_2$, from said pivot axis;
   wherein $R_2 > R_1$.

2. The optical analyzer of claim 1, wherein said actuator comprises an actuator screw that is linearly extended or retracted by rotation of the screw, and wherein said actuator screw has a tip that is coupled to the lens holder.

3. The optical analyzer of claim 2, wherein said tip of said actuator screw is coupled to said lens holder through a magnetic coupling.

4. The optical analyzer of claim 1, wherein $R_2$ is $> 2 \cdot R_1$.

5. The optical analyzer of claim 1, wherein $R_2$ is $> 3 \cdot R_1$.

* * * * *